(12) United States Patent
Hamilton

(10) Patent No.: US 7,749,175 B2
(45) Date of Patent: Jul. 6, 2010

(54) APPARATUS AND METHOD FOR STEERING A GUIDEWIRE AND CONNECTING TO AN EXTENSION GUIDEWIRE

(75) Inventor: Peter A. Hamilton, East Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/390,059

(22) Filed: Feb. 20, 2009

(65) Prior Publication Data

US 2009/0192462 A1 Jul. 30, 2009

Related U.S. Application Data

(60) Continuation of application No. 11/144,698, filed on Jun. 6, 2005, now Pat. No. 7,513,878, which is a continuation of application No. 10/316,043, filed on Dec. 11, 2002, now Pat. No. 6,916,293, which is a division of application No. 09/451,110, filed on Nov. 30, 1999, now Pat. No. 6,511,470.

(51) Int. Cl.
*A61B 19/00* (2006.01)

(52) U.S. Cl. ............... 600/585; 604/166.01; 604/528

(58) Field of Classification Search .......... 600/433, 600/434, 585; 604/166.01, 164.13, 528
See application file for complete search history.

(56) References Cited

U.S. PATENT DOCUMENTS

| | | | |
|---|---|---|---|
| 4,726,369 A | 2/1988 | Mar | |
| 4,858,810 A | 8/1989 | Intlekofer et al. | |
| 4,907,332 A | 3/1990 | Christain et al. | |
| 4,922,923 A | 5/1990 | Gambale et al. | |
| 5,133,364 A | 7/1992 | Palermo et al. | |
| 5,161,534 A | 11/1992 | Berthiaume | |
| 5,191,888 A | 3/1993 | Palmer et al. | |
| 5,234,002 A | 8/1993 | Chan | |

(Continued)

FOREIGN PATENT DOCUMENTS

WO  WO 97/18850  5/1997

*Primary Examiner*—Max Hindenburg
*Assistant Examiner*—Jonathan M. Foreman
(74) *Attorney, Agent, or Firm*—Crompton, Seager & Tufte, LLC

(57) ABSTRACT

An apparatus for steering a guidewire and for connecting the guidewire to an extension guidewire. The apparatus includes a steering device for gripping an exterior of the guidewire, the steering device defining a passageway therein through which the guidewire may pass; and a connecting device for connecting the guidewire to the extension guidewire. The connecting device is configured for mating with the steering device to form an integral unit. The invention further includes a method of inserting a guidewire in a body and connecting the guidewire to an extension guidewire. The method includes the steps of: providing an integral guidewire holder and tool for connecting a guidewire to an extension guidewire; gripping the guidewire with the integral guidewire holder; inserting the guidewire into a body lumen; displacing the integral guidewire holder and tool relative to the guidewire so that the proximal end of the guidewire is located in a slot of the integral guidewire holder and tool; inserting an extension guidewire into the slot of the integral guidewire holder and tool; and connecting the guidewire to the extension guidewire. The method further includes the step of aligning the guidewire and extension guidewire in the slot prior to the connecting step.

20 Claims, 5 Drawing Sheets

U.S. PATENT DOCUMENTS

| | | |
|---|---|---|
| 5,282,479 A | 2/1994 | Havran |
| 5,295,492 A | 3/1994 | Sellers |
| 5,312,338 A | 5/1994 | Nelson et al. |
| 5,325,746 A | 7/1994 | Anderson |
| 5,361,777 A | 11/1994 | Sellers |
| 5,392,778 A | 2/1995 | Horzewski |
| 5,507,300 A | 4/1996 | Mukai et al. |
| 5,634,475 A | 6/1997 | Wolvek |
| 5,851,189 A | 12/1998 | Forber |
| 5,971,991 A | 10/1999 | Sunderland |
| 6,039,700 A | 3/2000 | Sauter |

APPARATUS AND METHOD FOR STEERING A GUIDEWIRE AND CONNECTING TO AN EXTENSION GUIDEWIRE

This is a continuation of application Ser. No. 11/144,698 filed Jun. 6, 2005 now U.S. Pat. No. 7,513,878, which is a continuation of application Ser. No. 10/316,043, filed Dec. 11, 2002, now U.S. Pat. No. 6,916,293, which is a division of application Ser. No. 09/451,110, filed on Nov. 30, 1999, now U.S. Pat. No. 6,511,470, all of which are relied upon and incorporated herein by reference.

BACKGROUND OF THE INVENTION

1. Field of the Invention

This invention relates to an apparatus and method for manipulating a guidewire and connecting the guidewire to an extension guidewire.

2. Description of the Related Art

Medical guidewires generally are used for navigating through internal passageways of a body. The distal end of a guidewire is introduced into a body by a physician through an opening in the body. The physician manipulates the tip of the guidewire through the body to a site to be treated. A catheter or other medical device is usually advanced over the guidewire to the treatment site. In some medical applications, it is desirable to use multiple catheters sequentially in order to complete the medical procedure. When it is necessary to change catheters, it is usually preferred that the catheter be removed in a manner which enables a guidewire to remain in place in the body so that the end of the guidewire remains on the site to be treated. In order to maintain a guidewire in place while withdrawing the catheter, the guidewire must be gripped at its proximal end to prevent it from being pulled away from the site to be treated, for example, a blood vessel. However, the guidewire typically only extends for a short portion outside of the catheter which is inserted in the body. Therefore, before the catheter is fully withdrawn from the body, the catheter completely covers the proximally extending end of the guidewire. As a result, there is no way in which to grip the proximal end of the guidewire to hold it in place and prevent it from being withdrawn together with the catheter.

One method which has been proposed for solving the above catheter exchange problem is the use of an exchange wire. In such a method, the existing guidewire is removed and replaced by a longer exchange wire. The removal and replacement occurs with the existing catheter in place. Unfortunately, the insertion of each additional wire significantly increases the risk of trauma and puncture to the patient and extends the duration of the procedure.

Another common method is the use of an extension guidewire. This has improved the procedure for performing a catheter exchange. An extension guidewire allows a catheter exchange to be made without any guidewire exchanges. In this way, there is a significant reduction in risk of puncturing blood vessels in the body, and a reduction in the time to perform the procedure. However, current apparatus and methods for steering the main guidewire into the body and then connecting the main guidewire to an extension guidewire to perform a catheter exchange have certain drawbacks.

Current extension guidewire methods require the use of a separate apparatus for steering the main guidewire into the body and a separate apparatus for aligning and connecting the main guidewire with an extension guidewire. Typically, a torque vise or pin vise is provided for gripping the main guidewire and steering the main guidewire into the human body. The main guidewire is often provided with an angled tip so that the operator can rotate the main guidewire and steer the main guidewire through the body. The torque vise can be slid back along the main guidewire to permit advancement of the main guidewire relative to the torque vise in order to insert the main guidewire further into the human body. Once the main guidewire and catheter are in place, it is often necessary to perform a catheter exchange.

Typically, an alignment tool functions to connect the proximal end of the in-situ guidewire to an extension guidewire. The torque vise is first removed from the in-situ guidewire. The alignment tool is then placed on the in-situ guidewire and used to align and connect the in-situ guidewire with an extension guidewire. After the in-situ guidewire and extension guidewire are connected, the alignment tool is removed. The alignment tool is removed by sliding the alignment tool proximally over the portion of the in-situ guidewire located in the alignment tool and then over the extension guidewire. The existing catheter in the body is then drawn proximally over the entire length of the in-situ and extension guidewire, and then replaced by a new catheter by sliding the new catheter distally over the entire length of the extension guidewire and in-situ guidewire. The extension guidewire then can be disconnected once the new catheter is in place.

This process of using a separate torque vise and alignment tool is cumbersome and significantly increases the amount of time for performing such operations. The amount of time spent on such operations can significantly increase the risk to a patient. Moreover, the use of separate apparatus for steering the main guidewire and for connecting the main guidewire to an extension guidewire makes the operation more complex, thus leading to more opportunities for mistakes or movement of the in-situ main guidewire during a catheter exchange. In addition, each tool must be separately manufactured, packaged and handled, increasing cost, for example. Therefore, for the above reasons, the current apparatus and methods for steering a main guidewire and connecting the main guidewire to an extension guidewire are less than desirable. There is a need for an apparatus and method for steering a main guidewire and connecting the main guidewire to an extension guidewire which substantially obviates these problems.

SUMMARY OF THE INVENTION

The advantages and purposes of the invention will be set forth in part in the description which follows, and in part will be obvious from the description, or may be learned by practice of the invention. The advantages and purposes of the invention will be realized and attained by means of the elements and combinations particularly pointed out in the appended claims.

To attain the advantages and in accordance with the purposes of the invention, as embodied and broadly described herein, the invention includes an apparatus for steering a guidewire and for connecting the guidewire to an extension guidewire. The apparatus includes a steering device for gripping an exterior of the guidewire, the steering device defining a passageway therein through which the guidewire may pass, and a connecting device for connecting the guidewire to the extension guidewire. The connecting device is configured for mating with the steering device to form an integral unit.

In another aspect, the invention includes a method of inserting a guidewire into a body and connecting the guidewire to an extension guidewire. The method includes the steps of: providing an integral guidewire holder and tool for connecting a guidewire to an extension guidewire; gripping the guidewire with the integral guidewire holder; inserting the guidewire into a body lumen using the integral guidewire holder and tool; displacing the integral guidewire holder and tool relative to the guidewire so that the proximal end of the guidewire is located in a slot of the integral guidewire holder and tube; inserting an extension guidewire into the slot of the integral guidewire holder and tool; and connecting the guidewire to the extension guidewire.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Figure 1:
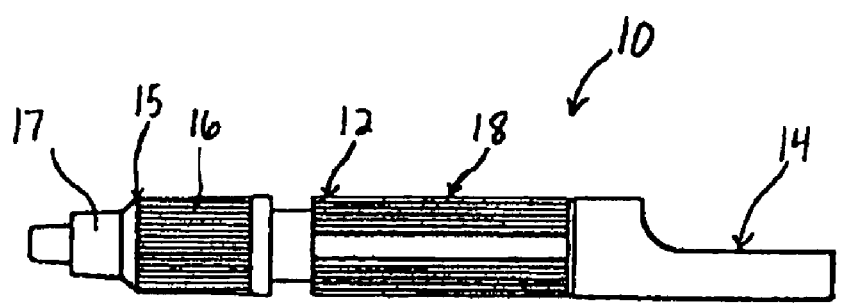
FIG. 1 is a side view of an apparatus for steering a guidewire and for connecting the guidewire to an extension guidewire according to an embodiment of the invention.
Figure 2:
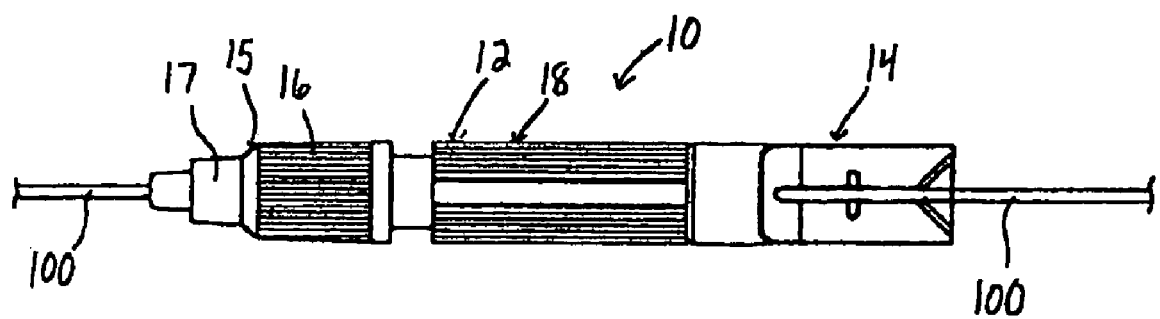
FIG. 2 is a top view of the apparatus of FIG. 1 with a guidewire inserted therethrough.
Figure 3:
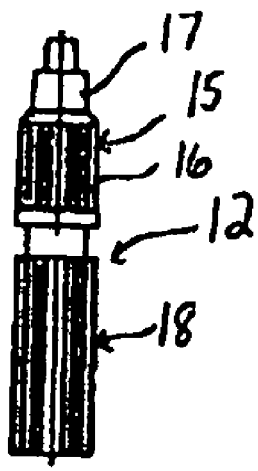
FIG. 3 is a side view of a steering device of the apparatus of FIG. 1.

Reference will now be made in detail to the present preferred embodiments of the invention, examples of which are illustrated in the accompanying drawings. Wherever possible, the same reference numbers will be used throughout the drawings to refer to the same or like parts.

Throughout the specification and claims, the terms "proximal" and "distal" are used to designate relative ends of components. These terms are used in the same manner in which they are widely used and well recognized by those knowledgeable in the field of medical procedures. The "distal" end of the components refers to the end furthest inside the body when in use and therefore furthest from the operator of the catheter or guidewire, whereas "proximal" end refers to the opposite end, i.e., the end closest to the operator.

In accordance with the present invention, an apparatus for steering a guidewire and for connecting the guidewire to an extension guidewire is provided. According to an embodiment of the invention, the apparatus generally includes a steering device and a connecting device. The steering device grips an exterior of the guidewire in order to steer the guidewire. The steering device defines a passageway therein through which a guidewire may pass. The connecting device connects the guidewire to an extension guidewire. The connecting device is configured for mating with the steering device to form a single integral unit. A method of steering the guidewire and connecting the guidewire to an extendable guidewire is also provided.

The apparatus for performing steering of a guidewire and connecting the guidewire to an extension guidewire will be described below. As embodied herein and shown in FIGS. 1-10, the apparatus 10 for steering a guidewire 100 and for connecting the guidewire to an extension guidewire includes a steering device 12 and a connecting device 14. The apparatus 10 is a single, integral unit which can be used for both steering a guidewire through lumens of a body, and for connecting an extension guidewire to the in-situ guidewire in order to perform a catheter exchange. With the present invention, it is not necessary to completely remove a torque vise from the guidewire prior to aligning and connecting the guidewire with an extension guidewire, as will be apparent from the following description. The provision of the steering device and connecting device into a single, integral unit simplifies the procedure for exchanging catheters, making the procedure quicker, safer, and less expensive.

In accordance with the present invention, the steering device manually grips the exterior of a guidewire in order to steer the guidewire through the body. As embodied herein and shown in FIGS. 1-6, the guidewire steering device 12 holds or grips an exterior of a guidewire 100. A guidewire steering device or guidewire holder can be any suitable device for holding onto a guidewire so that it can be manipulated through the body. In the specific embodiment shown in the drawings, the guidewire steering device or guidewire holder is a torque device often referred to as a torque vise or pin vise.

The steering device 12 comprises a distal outer tubular member 15 and an inner member 18. The distal outer tubular member 15 includes a proximal gripping portion 16 and a distal prong-engaging portion 17. The proximal gripping portion 16 has grooves on the outer periphery thereof for enhancing the ability of the operator to grip the distal outer tubular member 15. The distal prong-engaging portion 17, in one embodiment, has a smaller diameter than the proximal gripping portion. The details of the distal outer tubular member 15 will be described below in relation to the inner member 18.

Figure 4:
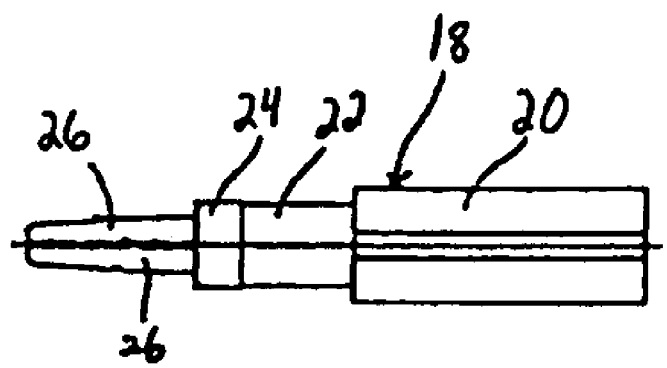
FIG. 4 is a side view of the steering device of FIG. 3 with portions removed.
Figure 5:
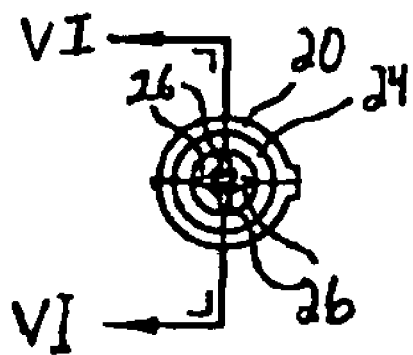
FIG. 5 is an end view of the steering device of FIG. 3.
Figure 6:
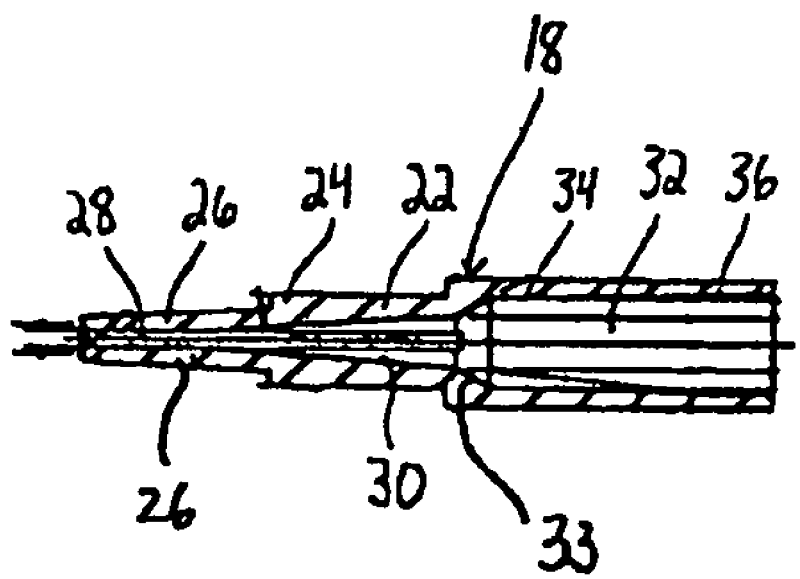
FIG. 6 is a cross-sectional view of the steering device of FIG. 3, taken along line VI-VI of FIG. 5.
Figure 7:
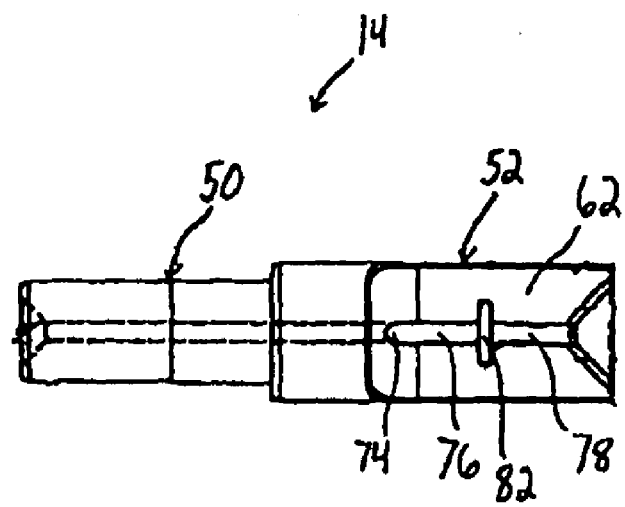
FIG. 7 is a top view of a connecting device of the apparatus of FIG. 1.
Figure 8:
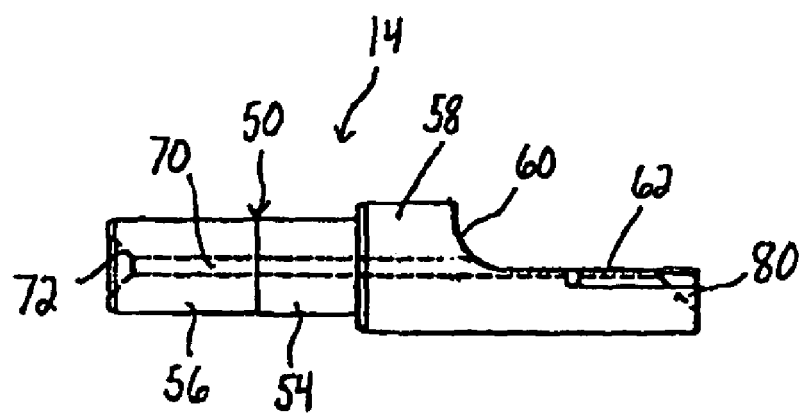
FIG. 8 is a side view of the connecting device of FIG. 7.
Figure 9:
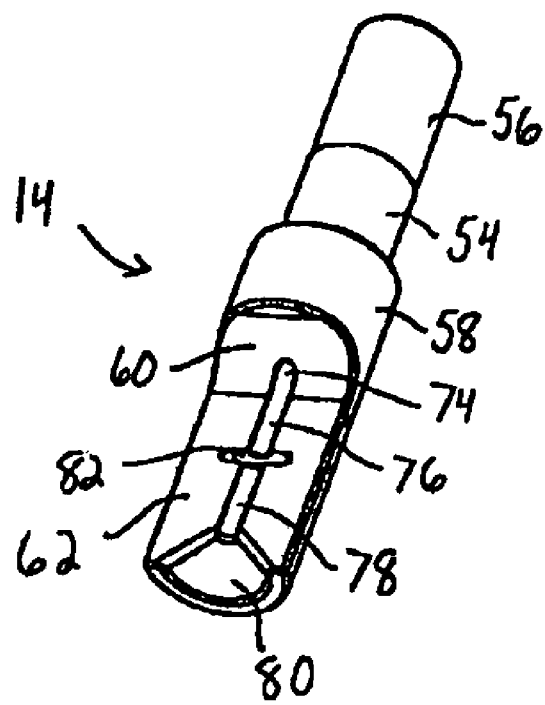
FIG. 9 is a perspective view of the connecting device of FIG. 7.
Figure 10:
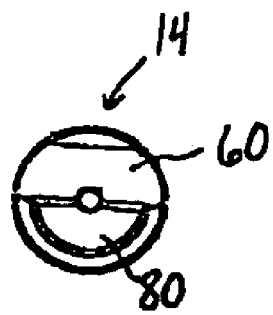
FIG. 10 is an end view of the connecting device of FIG. 7.

The inner member 18 includes a proximal cylindrical portion 20, a central cylindrical portion 22, a distal cylindrical portion 24, and a plurality of longitudinal prongs 26. As shown in FIGS. 4-6, the proximal cylindrical portion 20 has a greater diameter than the central and distal cylindrical portions 22 and 24, while the distal cylindrical portion 24 has a greater diameter than the central cylindrical portion 22. The distal outer tubular member 15 and the inner member 18 share a common axis and are slidable relative to one another. The distal outer tubular member 15 is positioned around the exterior of at least a portion of the central cylindrical portion 22, distal cylindrical portion 24, and the plurality of longitudinal prongs 26. The proximal gripping portion 16 of the distal outer tubular member 15 is primarily located around central cylindrical portion 22 and distal cylindrical portion 24.

The distal prong-engaging portion 17 of the distal outer tubular member 15 is located around the plurality of longitudinal prongs 26. The inner diameter of the distal prong-engaging portion 17 is configured to be slightly larger than the outside diameter of the plurality of longitudinal prongs 26 at the distal end of the prongs, but smaller than the outside diameter of the plurality of longitudinal prongs 26 at the proximal end of the prongs. Therefore, the axial sliding of the distal outer tubular member 15 in the proximal direction (to the right in FIGS. 1-2) causes the inner diameter of the distal prong-engaging portion 17 to interfere with the outer diameter of the plurality of longitudinal prongs 26. As the distal outer tubular member 15 is gradually slid farther in the proximal direction, the inner diameter of distal tubular member 15 will squeeze against the longitudinal prongs 26 to force the prongs to bend or compress toward each other. The bending and compressing narrows the gap between the prongs 26, ultimately forcing prongs 26 against guidewire 100 which is inserted inside a longitudinal passage 28 inside steering device 12. The mechanical manipulation of the distal outer tubular member 15 in the proximal direction will provide sufficient gripping force to secure the steering device 12 and guidewire 100 together in fixed relation to one another so that guidewire 100 can be steered through the human body. The manipulation of the distal outer tubular member 15 in the distal direction will release the grip of the longitudinal prongs 26 on guidewire 100, and allow for relative movement between the steering device and guidewire 100.

The scope of the present invention includes types of guidewire steering devices other than the torque-vise type device shown and described. For example, many different torque devices, such as a pin-vise with a chuck collet, exist where an outer member is rotated relative to an inner member in order to tighten or widen a plurality of longitudinal prongs similar to those shown in FIGS. 1-6. The type of torque device is not essential as long as the torque device is configured for mating with an alignment and connecting device of the present invention. Many torque vises have an open area on the proximal end capable of accepting an alignment and connecting device of the present invention.

The steering device of the present invention is configured for mating with an alignment and connecting device as will be described below. As shown in FIG. 6, the longitudinal passage 28 of the present embodiment tapers to becomes progressively larger along the central cylindrical portion 22 moving in the proximal direction (to the right in FIG. 6). The longitudinal passage 28 includes a conical passage 30 inside the central cylindrical portion 22. The conical passage 30 leads to a proximal passage 32 adjacent the proximal cylindrical passage 20. The proximal passage 32 includes a frustoconical section 33 at its most distal end adjacent passage 30, and a cylindrical portion 34 at the proximal end of section 33. Portion 34 includes a slight taper at a proximal portion 36. The diameter of the proximal portion 36 increases progressively towards the proximal end of the steering device 12. The proximal passage 32 is configured to mate with an alignment and connection tool, as will be described. It should be understood that the scope of the present invention includes any suitable configuration for mating the steering device with the alignment and connecting device is acceptable.

In accordance with the present invention, the apparatus for steering a guidewire and for connecting the guidewire to an extension guidewire includes an alignment and connecting device. As embodied herein and shown in FIGS. 1-2 and 7-10, an alignment and connecting device 14 for aligning and connecting the guidewire to an extension guidewire is provided. The connecting device 14 includes an attachment portion 50 configured for attaching the connecting device 14 to the guidewire steering device 12 to form a single unit, and an alignment portion 52 for aligning the guidewire with an extension guidewire. In some instances, the connecting device 14 and the guidewire steering device 12 may share a common axis when attached.

The attachment portion 50 of the connecting device 14 is configured to mate with the proximal passage 32 of the guidewire steering device 12, such that the attachment portion 50 of the connecting device 14 may be substantially adjacent to the proximal passage 32 of the guidewire steering device 12. The attachment portion 50 is generally cylindrical shaped with two cylindrical portions 54 and 56. The first cylindrical portion 54 extends from the alignment portion 52 of the connecting device 14. The second cylindrical portion 56 extends from the first cylindrical portion 54. In the preferred embodiment, the second cylindrical portion 56 has a slightly smaller diameter than the first cylindrical portion 54. The size and shape of the attachment portion can be of any of a large variety of sizes and shapes, as long as the attachment portion mates with a corresponding portion of the steering device. The attachment portion 50 is preferably adhesive bonded to the proximal passage of the steering device in order to provide a secure connection. Other acceptable attachment methods include, but are not limited to, a solvent bond, spin weld, vibration weld, and press-fitting. It is conceivable that a number of different types of fasteners could also be utilized for attaching the connecting device to the steering device.

The method for attaching the connecting device to the steering device depends on a variety of design considerations, including the materials that are used for the connecting device and steering device. In a preferred embodiment, the connecting device and steering device are both made out of nylon. Other acceptable materials include, but are not limited to, high density polyethylene, ABS (acetyl butidene styrene), various metals such as brass or stainless steel, and combinations of metals and plastics such as using brass prongs in a steering device with a plastic housing.

The connecting device 14 further includes an alignment portion 52. The alignment portion includes a cylindrical portion 58 that is connected to the attachment portion 50. In the embodiment shown in FIGS. 1-2 and 7-10, the diameter of the cylindrical portion 58 is greater than the diameter of the adjacent first cylindrical portion 54 so that portion 58 rests against the proximal end of the steering device. The cylindrical portion 58 of the attachment portion leads to a tapered portion 60. The taper is in the form of radius of a circle of a given diameter. The tapered portion 60 leads to substantially flat surface 62. The substantially flat surface 62 is located on a cutaway portion of a cylinder with an identical axis and diameter as the cylindrical portion 58 of the attachment portion 52. The substantially flat surface 62 extends along the axis of the attachment portion 52.

The connecting device 14 further includes a cylindrical longitudinal passage 70 which passes through the first and second cylindrical portions 54 and 56 of the attachment portion 50 and through the cylindrical portion 58 of the alignment portion 52. The longitudinal passage 70 begins at the distal end of the second cylindrical portion 56. The second cylindrical portion 56 is provided with a first conical opening 72 for the guidewire. The first conical opening 72 makes it easier for a guidewire to be inserted into the longitudinal passage 70 if the guidewire is slightly off center from the axis of the passage 70. The conical opening 72 narrows as it progresses away from the distal end of the attachment portion until the diameter of the opening 72 matches the diameter of the longitudinal passage 70. It is desirable for the diameter of the longitudinal passage 70 to be slightly larger than the largest diameter of the in-situ guidewire and extension guidewire that will be used.

The longitudinal passage 70 passes through the second cylindrical portion 56 of the attachment portion 50, first cylindrical portion 54 of the attachment portion 50, and cylindrical portion 58 of the alignment portion 52. The longitudinal passage 70 then passes into the tapered portion 60 and flat surface 62 as best shown in FIGS. 7-10. The passage 70 turns into a longitudinal slot after the tapered portion 74 of the passage. The longitudinal slot includes a first slot 76 located adjacent the tapered portion 74 and a second slot 78 located closer to the proximal end of the alignment portion 52. In the preferred embodiment, the longitudinal passage 70, tapered portion 74 of the passage, first slot 76, and second slot 78 all share a common axis and have identical diameters. Alternative embodiments for the longitudinal slots are envisioned and will be discussed below. In some instances, the longitudinal passage 70 of connecting device 14 and passage 32 of the guidewire steering device 12 maybe substantially adjacent and coaxial when attached. For example, the longitude passage 70 and passage 32 may share a common axis.

As embodied herein and shown in FIGS. 7-10, the second longitudinal slot 78 leads to a second conical opening 80 on the proximal end of the alignment portion 52. The second conical opening 80 tapers outwardly in order to facilitate insertion of the extension guidewire into the connecting device 14. The second conical opening 80 allows for the passage of the extension guidewire into the second longitudinal slot 78 even if the extension guidewire is slightly off center from the axis of the slot.

As embodied herein and shown in FIGS. 2 and 7-10, a transverse channel 82 is provided between the first longitudinal slot 76 and the second longitudinal slot 78. The transverse channel 82 extends perpendicular to the first and second longitudinal slots 76, 78. In the preferred embodiment, the transverse channel 82 has walls of an identical height, however, other configurations are within the scope of the invention. In the preferred embodiment, the transverse channel 82 has a depth greater than the depth of the longitudinal slots, however other configurations may also be envisioned and still be within the scope of this invention. The transverse channel serves several purposes. First, the transverse channel 82 serves as a reference point so that it is clear to the user where the connection between the in-situ guidewire and extension guidewire should be made. Second, in an embodiment where the walls of the transverse channel are of different heights, the higher wall may serve as a stop for the main guidewire or extension guidewire as it is inserted into the connecting device 14. This alternate embodiment will be discussed in the paragraph below. Lastly, the transverse channel 82 provides an area in which the guidewire and extension guidewire may be moved relative to one another to align with one another.

In one embodiment, the transverse channel has walls of differing height. This configuration would be useful in an arrangement where the main guidewire and extension guidewire have different diameters. The longitudinal slot for the wire having the larger diameter will also need to be of larger diameter. As the larger diameter wire is inserted into the alignment tool along its corresponding longitudinal slot, it will traverse the transverse channel and abut against the farthest vertical wall of the transverse channel, thereby impeding movement of the larger diameter wire. The end of the smaller guidewire can then be slid into the end of the end of the larger diameter wire because the ends of the wires are aligned.

Alternately, the transverse channel may be replaced by a simple straight line marked on the top of the flat surface where the transverse channel was previously located. This straight line will serve as a reference point for the operator. The operator can use the straight line as the point at which the guidewire should not be inserted any further into the alignment and connecting device. In an additional embodiment, the transverse channel consists of a slot with an identical depth as the first and second longitudinal slots.

A variety of different types of guidewires and extension guidewires may be used with the present invention. An exemplary type of extension guidewire connection is shown, for example, in U.S. Pat. No. 5,133,364, to Palermo et al., the complete disclosure of which is hereby incorporated by reference herein. U.S. Pat. No. 5,133,364 describes the extension guidewire connection in greater detail. In a preferred embodiment of the present invention, the main guidewire and extension guidewire have identical diameters. As described in U.S. Pat. No. 5,133,364, the proximal end of the main guidewire may be fitted with a tubular member having approximately the same outside diameter as the guidewire. The tubular member will be referred to as a hypotube because it is typically formed from commercially available hypodermic tubing. The hypotube typically has a wall thickness of the order of 0.003" and defines a cylindrical internal socket. The hypotube is considered to be part of the main guidewire because it is essentially permanently attached to the proximal end of the main guidewire. The hypotube is typically welded, bonded, or brazed to the main guidewire. Other suitable attachment methods are also acceptable.

In a preferred type of extension guidewire, the distal end of the extension guidewire has a smaller diameter than the remainder of the extension guidewire, and is provided with a helical coil on this smaller diameter portion, as also described in U.S. Pat. No. 5,133,364. The outer diameter of the helical coil is equal to or just slightly greater than the inner diameter of the cylindrical internal socket of the hypotube. This provides a light interfering fit with the socket. The main guidewire and extension guidewire are connected by inserting the distal end of the extension guidewire into the cylindrical internal socket of the main guidewire and twisting. The extension guidewire can be inserted into the guidewire as described in U.S. Pat. No. 5,133,164. The friction fit between the helical coil and the internal socket can withstand a relatively large amount of axial tension without becoming disconnected. However, the extension guidewire can be easily disconnected by simply twisting the extension guidewire in the appropriate direction.

The mating ends of the main and extension guidewires may take a variety of other structural forms known in the art and still be within the scope of the present invention. The invention is not limited by the particular guidewire and, particularly, the particular guidewire structure for connecting the ends. For example, the extension guidewire can be press-fit into a cylindrical opening in the main guidewire. Alternately, the proximal end of the main guidewire and the distal end of the extension guidewire may be provided with mating geometrical shapes such as hexagon ends.

The method of steering the guidewire and connecting the main guidewire to an extension guidewire of the present invention will now be described. The method of the present invention is useful in a wide variety of medical procedures, including, for example, vascular applications such as angioplasty and nonvascular applications such as a biliary procedure. Other procedures include cardiology procedures such as stent placements, neuro-radiology procedures such as placement of coils, and urological procedures such as a catheter placement to remove stones. In a biliary procedure, for example, a cannula is passed through the mouth into the common bile duct. The present invention can be used, for example, to insert balloon or basket catheters to remove gallstones.

The main guidewire may be steered into place in a lumen of the body by placing the guidewire through the steering device 12 of the apparatus 10. While gripping the guidewire, the steering device can be manipulated to change the angle and speed of entry into the body. If the guidewire has an angled tip, the guidewire can be rotated in order to change the direction that the guidewire will follow in the body. The guidewire is then fed from the steering device 12 by a progressive gripping and releasing of the distal end of the steering device 12. Each gripping and releasing will advance the guidewire slightly farther into the body. An initial guide catheter may already be inserted in the body, or the catheter may be inserted over the guidewire after the guidewire has obtained the desired position. Once a catheter is in place and it is desirable to remove the catheter to replace it with another catheter, an extension guidewire can be connected to the in-situ guidewire.

An extension guidewire may be attached to the guidewire as follows. First, the apparatus 10 is moved proximally along the guidewire so that it is positioned on the proximal end of the in-situ guidewire. The in-situ guidewire is arranged so that the proximal end of the in-situ guidewire passes through the longitudinal passage 28 of the steering device 12 and the longitudinal passage 70 of the connection device 14. The apparatus 10 then is slid until the proximal end of the in-situ guidewire is lined up with the transverse channel 82. If the transverse channel 82 has walls of varying height, the proximal end of the in-situ guidewire can be positioned so that it is flush with the wall adjacent the second longitudinal slot 78.

The steering device 12 is then clamped onto the main guidewire and the extension guidewire is inserted into the second conical opening opening 80 of the connection device 14. The extension guidewire is slid along the second longitudinal slot 78 until the distal end of the extension guidewire abuts and is inserted in the proximal end of the main guidewire, or attached to the main guidewire by another method.

After the extension guidewire is connected to the main guidewire by the appropriate method, the steering device 12 may be released so that it no longer firmly grips the main guidewire, and the apparatus 10 can be slid off of the main guidewire and extension guidewire. The existing catheter can then be removed by pulling the catheter over the length of the main guidewire and extension guidewire. A new catheter may then be inserted by pushing the new catheter over the length of the extension guidewire and main guidewire. The extension guidewire can then be disconnected. In order to disconnect, the apparatus 10 can be fed over the length of the extension guidewire to the point just before the connection. The main guidewire is held firm. The apparatus 10 can then be used to grip the extension guidewire so that the extension guidewire can be rotated relative to the main guidewire. The above steps can be repeated in order to exchange a plurality of catheters.

It will be apparent to those skilled in the art that various modifications and variations can be made in the apparatus and method for steering a guidewire and for connecting a guidewire to an extension guidewire, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for steering a guidewire and for connecting the guidewire to an extension guidewire, comprising:
   a steering device configured to grip the guidewire, the steering device including a passageway therein configured to receive the guidewire; and
   a connecting device configured to connect the guidewire to the extension guidewire, wherein said connecting device and said steering device share a common longitudinal axis, said connecting device configured to slidably mate with said steering device to form an integral unit;
   wherein a distal end of the connecting device adjacent the steering device includes a conical opening for guiding the guidewire into a passageway of the connecting device and the passageway of said connecting device transitions into a longitudinal slot at a tapered portion of said connecting device.

2. The apparatus of claim 1, wherein said steering device includes a plurality of prongs configured to grip the guidewire.

3. The apparatus of claim 2, wherein the steering device includes an outer member and an inner member, the outer member including a gripping portion and a prong-engaging portion, the inner member including a proximal cylindrical portion, a central cylindrical portion, a distal cylindrical portion, and the plurality of prongs.

4. The apparatus of claim 3, wherein the outer member is positioned around an exterior of at least a portion of the central cylindrical portion, the distal cylindrical portion, and the plurality of prongs.

5. The apparatus of claim 4, wherein the outer member and the inner member share a common axis and are slidable relative to one another, and an axial sliding of the outer member causes an inner surface of the prong-engaging portion to interfere with an outer surface of the plurality of prongs, causing the plurality of prongs to move toward each other.

6. The apparatus of claim 1, wherein said connecting device includes a longitudinal slot for aligning the guidewire with the extension guidewire.

7. The apparatus of claim 6, wherein a proximal end of the connecting device farthest from the steering device includes a partial conical opening for guiding the extension guidewire into the longitudinal slot.

8. The apparatus of claim 1, wherein the tapered portion terminates at a substantially flat surface, the longitudinal slot being located in the substantially flat surface, the substantially flat surface including a transverse channel intersecting said longitudinal slot.

9. The apparatus of claim 8, wherein a first wall of the transverse channel is higher than a second wall of the transverse channel.

10. The apparatus of claim 1, wherein the passageway of said steering device tapers to become progressively larger as it approaches an end of said steering device that mates with said connecting device.

11. An apparatus for steering a guidewire and for connecting the guidewire to an extension guidewire, comprising:
    a steering device configured to grip the guidewire, the steering device including a passageway therein configured to receive the guidewire and a plurality of prongs configured to grip the guidewire; and
    a connecting device configured to connect the guidewire to the extension guidewire, wherein said connecting device includes a passageway configured to receive the guidewire, the passageway of the steering device and the passageway of the connecting device being substantially adjacent and coaxial, said connecting device configured to mate with said steering device to form an integral unit;
    wherein the steering device includes an outer member and an inner member, outer member including a gripping portion and a prong-engaging portion, the inner member including a proximal cylindrical portion, a central cylindrical portion, a distal cylindrical portion, and the plurality of prongs.

12. The apparatus of claim 11, wherein said passageway of the connecting device extends to a longitudinal slot configured to align the guidewire with the extension guidewire.

13. The apparatus of claim 12, wherein the slot is located in a substantially flat surface, the substantially flat surface including a transverse channel intersecting said longitudinal slot.

14. The apparatus of claim 13, wherein a first wall of the transverse channel is higher than a second wall of the transverse channel.

15. The apparatus of claim 11, wherein the connecting device includes a cylindrical outer surface configured to slidably mate with a cylindrical inner surface of the steering device.

16. The apparatus of claim 11, wherein a distal end of the connecting device adjacent the steering device includes a conical opening for guiding the guidewire into the passageway of the connecting device.

17. The apparatus of claim 11, wherein the outer member and the inner member share a common axis and are slidable relative to one another, and an axial sliding of the outer member causes an inner surface of the prong-engaging portion to interfere with an outer surface of the plurality of prongs, causing the plurality of prongs to move toward each other.

18. An apparatus for steering a guidewire and for connecting the guidewire to an extension guidewire, comprising:
    a steering device configured to grip the guidewire, the steering device including a passageway therein configured to receive the guidewire; and
    a connecting device configured to connect the guidewire to the extension guidewire, said connecting device being configured to mate with said steering device along a common axis to form an integral unit, wherein said connecting device includes a longitudinal slot for aligning the guidewire with the extension guidewire;
    wherein the steering device includes an outer member and an inner member, the outer member including a gripping portion and a prong-engaging portion, the inner member including a proximal cylindrical portion, a central cylindrical portion, a distal cylindrical portion, and a plurality of prongs.

19. The apparatus of claim 18, wherein the slot is located in a substantially flat surface, the substantially flat surface including a transverse channel intersecting said longitudinal slot.

20. The apparatus of claim 18, wherein the outer member and the inner member share a common axis and are slidable relative to one another, and an axial sliding of the outer member causes an inner surface of the prong-engaging portion to interfere with an outer surface of the plurality of prongs, causing the plurality of prongs to move toward each other.

* * * * *

UNITED STATES PATENT AND TRADEMARK OFFICE
CERTIFICATE OF CORRECTION

PATENT NO.        : 7,749,175 B2                                               Page 1 of 1
APPLICATION NO.   : 12/390059
DATED             : July 6, 2010
INVENTOR(S)       : Peter A. Hamilton It is certified that error appears in the above-identified patent and that said Letters Patent is hereby corrected as shown below:

Column 10
Line 63: after "inner member," and before "outer member", insert -- the --.

Signed and Sealed this

Fourteenth Day of September, 2010

David J. Kappos
*Director of the United States Patent and Trademark Office*